(12) United States Patent
Gnade et al.

(10) Patent No.: US 7,288,171 B2
(45) Date of Patent: Oct. 30, 2007

(54) METHOD FOR USING FIELD EMITTER ARRAYS IN CHEMICAL AND BIOLOGICAL HAZARD MITIGATION AND REMEDIATION

(75) Inventors: Bruce E. Gnade, Lewisville, TX (US); Robert M. Wallace, Richardson, TX (US)

(73) Assignee: University of North Texas, Denton, TX (US)

( * ) Notice: Subject to any disclaimer, the term of this patent is extended or adjusted under 35 U.S.C. 154(b) by 734 days.

(21) Appl. No.: 10/051,970

(22) Filed: Jan. 18, 2002

(65) Prior Publication Data
US 2003/0136660 A1    Jul. 24, 2003

(51) Int. Cl.
*B01J 19/08*    (2006.01)
(52) U.S. Cl. ...................... 204/164; 588/227
(58) Field of Classification Search ........... 204/164; 558/227; 588/227
See application file for complete search history.

(56) References Cited

U.S. PATENT DOCUMENTS

| | | | |
|---|---|---|---|
| 5,729,086 A | 3/1998 | Jeong et al. | 313/495 |
| 5,788,551 A | 8/1998 | Dynka et al. | 445/25 |
| 5,827,102 A | 10/1998 | Watkins et al. | 445/25 |

OTHER PUBLICATIONS

Chalamala et al. ("Effect of CH4 on the electron emission characteristics of active molybdenum field emitter arrays", J. Vac. Sci. Technol. B 16(6), 1998, pp. 307-376.*

Chalamala et al. ("Effect of O2 on the electron emission characteristics of active molybdenum field emission cathode arrays", J. Vac. Sci. Technol. B, 16(5), pp. 2859-2865, 1998.*

Chalamala et al. ("Interaction of H2O with active Spindt-Type molybdenum field emitter arrays", J. Vac. Sci. Technol. B, 17(2), pp. 303-305, 1999.*

Material Safety Data Sheet (MSDS) of Molybdenum obtained from Alfa Aesar Co., May 30, 2000.*

MSDS of Methane obtained from Airgas Inc, Jan. 3, 2001).*

Swanson, "Field Emission," *Encyclopedia of Physics*, pp. 315-316 (1981).

Chalamala et al., "Interaction of $H_2O$ with Active Spindt-Type Molybdenum Field Emitter Arrays," *J. Vac. Sci. Technol. B* vol. 17:303-305 (1999).

Chalamala et al., "Surface Conditioning of Active Molybdenum Field Emission Cathode Arrays with $H_2$ and Helium," *J. Vac. Sci. Technol. B* vol. 16:2855-2858 (1998).

Chalamala et al., "Poisoning of Spindt-Type Molybdenum Field Emitter Arrays by $CO_2$," *J. Vac. Sci. Technol. B* vol. 16:2866-2870 (1998).

(Continued)

*Primary Examiner*—Kishor Mayekar
(74) *Attorney, Agent, or Firm*—Williams, Morgan & Amerson

(57) ABSTRACT

A method is provided, the method comprising operating a field emitter array (FEA) to generate at least one of a high electric field and a high electron flux, and exposing the field emitter array (FEA) to at least one gas. The method further comprises generating at least one radical species from the at least one gas exposed to the at least one of the high electric field and the high electron flux.

60 Claims, 10 Drawing Sheets

OTHER PUBLICATIONS

Chalamala et al., "Effect of $O_2$ on the Electron Emission Characteristics of Active Molybdenum Field Emission Cathode Arrays," *J. Vac. Sci. Technol. B* vol. 16:2859-2865 (1998).

Chalamala et al., "Effect of $CH_4$ on the Electron Emission Characteristics of Active Molybdenum Field Emitter Arrays," *J. Vac. Sci. Technol. B* vol. 16:3073-3076 (1998).

Wallace et al., "Effects of Residual Gas Exposures on the Emission Characteristics of Field Emission Arrays," *AVS National Symposium*, Abstract No. FP+VT-MoM3 (Oct. 25, 1999).

Gnade, "4. Description of Research," *1999 ARP Proposal* (Feb. 4, 2000).

Gnade et al., "Field Ionization Arrays for Biological and Chemical Warfare Detection and Actuation," *MIT UNT Proposal*, pp. 1-34 (Feb. 4, 2000).

Wallace et al., "Field Emission Displays and Vacuum Packaging Issues," *Flat Panel Display Topical Conference 46th AVS International Symposium* (1996).

* cited by examiner $I = aV^2\exp(-b\Phi^{3/2}/V)$ slope of F-N plot $(m) \propto \Phi^{3/2}$

```
810 ──┐   ┌─────────────────────┐
       │   │ Operate a low-power │
       │   │ field emission array│
800 ──┐│   │ (FEA) to generate a │
       └──▶│ high electric field │
           │ and/or a high       │
           │ electron flux       │
           └──────────┬──────────┘
                      ▼
           ┌─────────────────────┐
           │ Expose the low-power│
           │ field emission array│
           │ (FEA) to at least   │
           │ one gas             │──── 820
           └──────────┬──────────┘
                      ▼
830 ──┐    ┌─────────────────────┐
       └──▶│ Generate at least   │
           │ one radical species │
           │ from the gas exposed│
           │ to the high electric│
           │ field and/or the    │
           │ high electron flux  │
           └──────────┬──────────┘
                      ▼
           ┌─────────────────────┐
           │ React the radical   │
           │ species with at     │
           │ least one of a      │
           │ chemical and/or a   │
           │ biological toxin    │──── 840
           └─────────────────────┘
```

- 910: Operate a low-power field emission array (FEA) to generate a high electric field and/or a high electron flux
- 920: Expose the low-power field emission array (FEA) to at least one of a chemical and/or a biological toxin
- 930: Dissociate the chemical and/or the biological toxin exposed to the high electric field and/or the high electron flux

```
1010 ─┐  Operate a field emission
1000 ─┐   array (FEA) to generate a high
         electric field and/or a high
         electron flux
              │
              ▼
         Expose the field emission
         array (FEA) to at least one of
         a chemical and/or a biological
         toxin                              ── 1020
              │
              ▼
1030 ─┐  Ionize the chemical and/or
         the biological toxin exposed
         to the high electric field
         and/or the high electron flux
```

Figure 10

METHOD FOR USING FIELD EMITTER ARRAYS IN CHEMICAL AND BIOLOGICAL HAZARD MITIGATION AND REMEDIATION

BACKGROUND OF THE INVENTION

1. Field of the Invention

This invention relates generally to methods of using field ionization devices, and, more particularly, to a method for using field emitter arrays to mitigate and remediate chemical and biological hazards.

2. Description of the Related Art

One of the biggest threats to the military and civilian populations of the United States and the rest of the world is the use of weapons of mass destruction based on biological and chemical warfare. Research emphasis has been on the detection of biological weapons because of the potentially catastrophic nature of the use of biological weapons. Until recently, there has been less emphasis on chemical weapons because of the large volume of material typically required to pose a major threat. However, there is growing concern that terrorists, foreign or domestic, could attack chemical plants producing ammonia ($NH_3$), chlorine ($Cl_2$), insecticides, and the like, where there are large volumes of highly toxic materials. Additionally, there are many manufacturing facilities (for example, manufacturing plants that typically use arsine, germane, diborane, and the like) where there are also large volumes of highly toxic materials already in place that may be vulnerable to terrorist attack. Because of these and other similar potentially disastrous scenarios, chemical weapons again are a major concern.

One of the problems with many of the current schemes for biological warfare defense (BWD) and chemical warfare defense (CWD) is that the defense systems are specific to certain chemicals or pathogens. Schemes that provide a more general defense such as high temperature catalytic oxidation or radio frequency (RF) plasma oxidation, require a large amount of energy and power, and can produce harmful side-products. What is required is a defense system that can render harmless a large number of pathogens or compounds without producing harmful side-products. Another important element, especially for military applications is that the defense system should be portable and power-efficient enough so that the defense system can be used and implemented by individual soldiers and on small vehicles.

Biological and chemical warfare and/or terrorism and/or accidents are complicated by the fact that the delivery of the biological and/or chemical agents can be as simple as exposure of the pathogens and/or toxins to the atmosphere, resulting in potentially wide dispersal. Examples of these biological and/or chemical agents and/or pathogens and/or toxins may include Sarin (($CH_3$)$_2$CHOP(O)F$CH_3$), Soman (($CH_3$)$_3$CHC$H_3$OP(O)F$CH_3$), VX ($CH_3$P(O)O$C_2H_5$SC$H_2$C$H_2$N(CH($CH_3$)$_2$)$_2$), and the like. The delivery method can be simple and extremely low cost. The effect of the biological and/or chemical agent can be immediate, or it can be delayed for days. Conventional devices are expensive, slow, consume a lot of power, and are bulky. These devices cannot operate in real-time and are not suitable for battlefield and forward deployment or emergency situations. Conventional approaches that are fast and that have the potential for real-time operation are extremely agent-specific and can be thwarted by developing new biological and chemical warfare agents. Hence, new approaches that have the potential of instantaneous detection in the field that are low cost, portable and consume very little power are desired.

The present invention is directed to overcoming, or at least reducing the effects of, one or more of the problems set forth above.

SUMMARY OF THE INVENTION

In one aspect of the present invention, a method is provided, the method comprising operating a field emitter array (FEA) to generate at least one of a high electric field and a high electron flux, and exposing the field emitter array (FEA) to at least one gas. The method further comprises generating at least one radical species from the at least one gas exposed to the at least one of the high electric field and the high electron flux.

In another aspect of the present invention, a method is provided, the method comprising operating a low-power field emitter array (FEA) to generate at least one of a high electric field and a high electron flux, and exposing the low-power field emitter array (FEA) to at least one gas. The method further comprises generating at least one radical species from the at least one gas exposed to the at least one of the high electric field and the high electron flux, and reacting the at least one radical species with at least one of a chemical and a biological toxin.

In yet another aspect of the present invention, a method is provided, the method comprising operating a low-power field emitter array (FEA) to generate at least one of a high electric field and a high electron flux, and exposing the low-power field emitter array (FEA) to at least one of a chemical and a biological toxin. The method further comprises dissociating the at least one of the chemical and the biological toxin exposed to the at least one of the high electric field and the high electron flux.

In still yet another aspect of the present invention, a method is provided, the method comprising operating a field emitter array (FEA) to generate at least one of a high electric field and a high electron flux, and exposing the field emitter array (FEA) to at least one of a chemical and a biological toxin. The method further comprises ionizing the at least one of the chemical and the biological toxin exposed to the at least one of the high electric field and the high electron flux.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIGS. 1-10 schematically illustrate various embodiments of a method according to the present invention; and, more particularly:

FIG. 1 schematically illustrates a field effect display (FED) device representative of the principle of field emission;

FIG. 3 schematically illustrates the difference between the ionization from a field emitter array (FEA) and the ionization from a conventional electron impact ionization source (EIIS), under controlled vacuum conditions;

FIG. 4 schematically illustrates a comparison of the production of the atomic oxygen ion $O^+$ and molecular oxygen ion $O_2^+$ as a function of the molecular oxygen $O_2$ pressure;

FIG. 5 schematically illustrates a comparison of the production of the atomic oxygen ion $O^+$ and molecular oxygen ion $O_2^+$ as a function of gate voltage $V_g$;

FIG. 6 schematically illustrates a molybdenum-based field emitter array (FEA) exposed to helium, forming molybdenum-helide ions such as $MoHe^+$ and $MoHe_2^+$; and FIGS. 7-10 schematically illustrate respective flow charts for various illustrative embodiments of a method according to the present invention.

Figure 1:
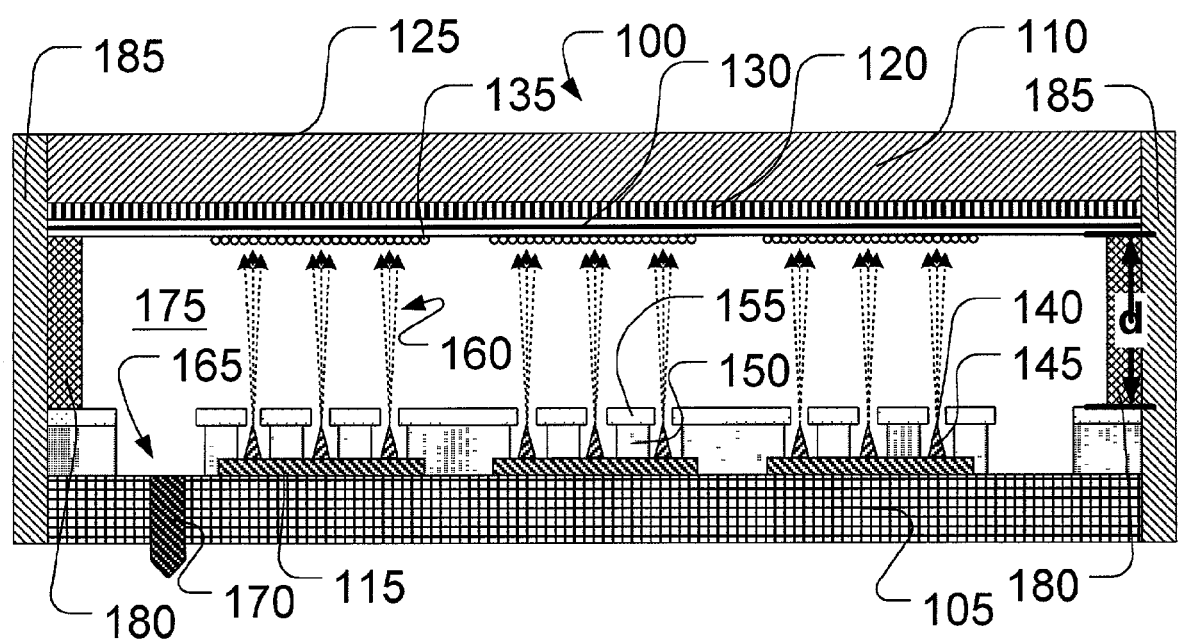

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In various illustrative embodiments of the present invention, high electric fields and electron flux densities generated by field emission arrays (FEAs) are used and employed for biological warfare defense (BWD) and chemical warfare defense (CWD) systems. Additionally, various illustrative embodiments of the present invention enable the chemistry of complex molecules in very high electric fields and high electron flux densities to be exploited and used in reaction channels that are otherwise unavailable at typical thermal energies.

Recent advances in field emission arrays (FEAs) now make it possible to utilize the chemistry of gaseous species in electric fields as high as about $10^7$-$10^8$ V/cm and with average electron current densities as high as about an Amp/cm². These conditions can be achieved with voltages of less than or equal to about 100 V because the cathode-to-gate distance in modern field emission arrays (FEAs) is less than or equal to about 1 micron (1 µm).

The principle of field emission may be illustrated by referring to a schematically illustrated field emission display (FED) device 100, as shown in FIG. 1. The field emission display (FED) device 100 has a base plate 105 and a face plate 110 opposite to the base plate 105. A number of cathode electrodes 115 are formed, in strips, for example, on the base plate 105. A number of anode electrodes 120 are formed, also in strips, for example, on the face plate 110. The strips of the anode electrodes 120 are disposed generally perpendicular to the strips of the cathode electrodes 115.

The anode electrodes 120 are formed on the face plate 110 on the surface opposite to a viewing surface 125, and are made of indium oxide, tin oxide, indium-tin-oxide (ITO), and the like, which are transparent, conductive materials. A fluorescent material layer 130, having phosphors 135 disposed thereon, is deposited on the anode electrodes 120. Electrons ejected from tips 140 of emitters 145 on the base plate 105 collide with the phosphors 135 in the fluorescent material layer 130 and excite electrons in the phosphors 135 into higher energy levels. As a result of the collision, light is emitted as the electrons in the phosphors 135 return to lower energy levels.

The base plate 105 is placed behind the face plate 110, away from the viewing surface 125, and is made of a semiconducting material or a ceramic or a glass. The cathode electrodes 115 formed on the base plate 105 are made of a highly doped semiconducting material such as polycrystalline silicon (polysilicon or poly) or a conductive metal. The emitters 145 are fabricated on the cathode electrodes 115 and are made of a metal such as molybdenum (Mo), tungsten (W), platinum (Pt), and the like. The emitters 145 may also be made of a semiconducting material such as silicon or silicon coated with titanium (Ti) or titanium nitride and/or any other convenient low work function material. The shape of the emitters 145 is generally conical, and electrons are emitted from the tips 140 of the emitters 145.

The emitters 145 may be separated from one another by dielectric materials 150 and gate electrodes 155 may be deposited on the dielectric materials 150. The gate electrodes 155 control an emission current 160 emitted from the emitters 145. Also, an opening 165 for evacuation is made at a desired portion of the base plate 105 where the cathode electrodes 115 are not deposited. An evacuation tube 170 is inserted into the opening 165 for evacuation (also known as "tubulation"). Gas residing in main space 175 is pumped out through the evacuation tube 170 and through the opening 165. When an appropriate low pressure is achieved, the evacuation tube 170 is sealed off.

The face plate 110 is attached facing the base plate 105 by spacers 180, with a desired separation distance d ranging from approximately 100 µm to 1000 µm, so that the fluorescent material layer 130 and the emitters 145 face each other and form the main space 175. The main space 175 is sealed off by firing the field emission display (FED) device 100 assembly after coating both side edges of the face plate 110 and base plate 105 with a frit seal 185.

The spacers 180 between the face plate 110 and the base plate 105 may have the shape of a wall at each of both edges of the face plate 110 and the base plate 105, and may have a cylindrical shape in between both edges of the face plate 110 and the base plate 105. The spacers 180 may be made of dielectric materials such as glass or polyimide, and the like.

The spacers 180 should have sufficient strength to withstand the load caused by the high pressure differential that exists between external atmospheric pressure and the pressure within the evacuated main space 175. The spacers 180 should also make the spacing in the display panel even, for consistent image resolution and brightness.

Also, the cathode electrodes 115 and the anode electrodes 120 may be extended to connect to an external circuit (not shown) placed outside the main space 175.

In one illustrative embodiment of an field emission display (FED) device 100, as described in FIG. 1, if a negative voltage and a positive voltage are respectively applied to one of the cathode electrodes 115 and a corresponding one of the anode electrodes 120 by an external circuit, an electric field is established between that cathode electrode 115 and that anode electrode 120. Electrons are able to be emitted from the emitters 140 where such an electric field is formed. The voltage on the anode electrodes 120 may not cause field emission, since the electric field strength of the electric field established between a cathode electrode 115 and the corresponding anode electrode 120 may not be large enough. However, the anode electrodes 120 may attract electrons once emitted from the corresponding cathode electrodes 115.

Positive voltages are applied to selected ones of the gate electrodes 155 on the base plate 105 to make the emission of electrons from the corresponding emitters 145 easier. The electrons emitted from the emitters 145 are accelerated by the anode electrodes 120 and collide with the phosphors 135 of the fluorescent material layer 130. Then, the fluorescent material layer 130 emits light in the appropriate pattern for forming a picture viewable on the viewing surface 125.

The field emission display (FED) structure described in detail above, which is called triode-type, has conic-shaped emitters 145 made of metal, for example, and gate electrodes 155. Alternatively, a thin film diode-type field emission display (FED) structure is available where emitters are made of diamond thin-film and separate gate electrodes are not needed.

Figure 2A:
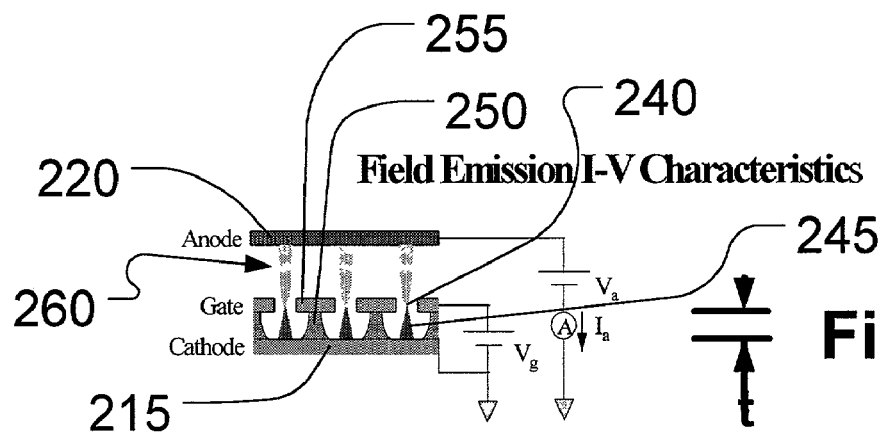
FIG. 2(a) schematically illustrates a small portion of a field emitter array (FEA) representative of those used in various of the illustrative embodiments of the present invention.

More generally, FIG. 2(a) shows a schematic illustration of a small portion of a field emitter array (FEA) representative of those used in various of the illustrative embodiments of the present invention. A cathode electrode 215 and an anode electrode 220 are disposed opposite each other, and may be made of indium oxide, tin oxide, indium-tin-oxide (ITO), and the like, for example, which are transparent, conductive materials. In alternative illustrative embodiments, the cathode electrode 215 and/or the anode electrode 220 may be made of highly doped polysilicon or a conductive material such as platinum (Pt), gold (Au), tin oxide ($SnO_2$), ITO, zinc oxide (ZnO), and the like. Electrons 260 are emitted from tips 240 of emitters 245 disposed on the cathode electrode 215. The emitters 245 are fabricated on the cathode electrodes 215 and are made of a metal such as molybdenum (Mo), tungsten (W), platinum (Pt), and the like. The emitters 245 may also be made of a semiconducting material such as silicon or silicon coated with titanium (Ti) or titanium nitride and/or any other convenient low work function (low $\Phi$) material. For example, carbon nanotubes may also be used for the emitters 245. The shape of the emitters 245 is generally conical, and electrons 260 are emitted from the tips 240 of the emitters 245.

The emitters 245 may be separated from one another by dielectric materials 250 and gate electrodes 255 may be deposited on the dielectric materials 250. The gate electrodes 255 control a field emission current of the electrons 260 emitted from the emitters 245. The electric field strengths at the tips 240 of the emitters 245 may be as high as about $10^7$-$10^8$ V/cm. The field emission current of the electrons 260 may have an average electron current density (flux) as high as about an Amp/$cm^2$. These conditions may be achieved with a gate voltage $V_g$ of less than or equal to about 100 V because the thickness t of the dielectric materials 250, in a field emission array (FEA), according to various illustrative embodiments of the present invention, is less than or equal to about 1 micron (1 μm). The thickness t of the dielectric materials 250 may also be substantially similar to the cathode-to-gate distance for gate openings of about 1 micron (1 μm).

In various alternative illustrative embodiments, a field emitter array (FEA) may be operated with a gate voltage $V_g$ of less than or equal to about 1000 V with single wire emitters 245. In various alternative illustrative embodiments, a field emitter array (FEA) may be operated with the cathode-to-gate distance and/or gate openings in a range of about 1 micron (1 μm) to about 1 millimeter (1 mm).

Figure 2B:
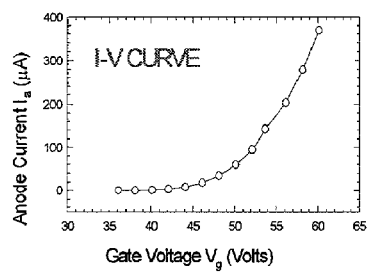
FIG. 2(b) schematically illustrates a current/voltage (I-V) curve for a modem molybdenum-based field emitter array with 1 micrometer gate openings.

The cathode electrode 215 and the anode electrode 220 may be extended to connect to an external circuit, as indicated schematically in FIG. 2(a). A positive gate voltage $V_g$ may be applied to the gate electrodes 255, while the cathode electrode 215 may be grounded, leading to the field emission current of the electrons 260. A positive anode voltage $V_a$ may be applied to the anode electrode 220, attracting the field emission current of the electrons 260, as measured by an ammeter A, measuring an anode current $I_a$, as shown graphically in FIG. 2(b). FIG. 2(b) shows a current/voltage (I-V) curve for a modern molybdenum-based field emitter array. The gate voltage $V_g$, measured in volts (V), is plotted along the horizontal axis against anode current $I_a$, measured in micro-Amperes (μA), plotted along the vertical axis.

Figure 2C:
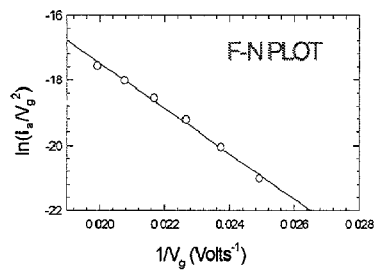
FIG. 2(c) schematically illustrates Fowler-Nordheim tunneling for a modem molybdenum-based field emitter array with 1 micrometer gate openings.

Ionizers based on electron impact ionization use the electrons 260 emitted from the field emission array (FEA). The array of sharp tips 240 which serve as the high flux electron 260 source as a result of Fowler-Nordheim tunneling, as shown graphically in FIG. 2(c). The Fowler-Nordheim tunneling anode current $I_a$, may be expressed as a function of the gate voltage $V_g$, and the work function $\Phi$ of the emitters 245 fabricated on the cathode electrode 215 as follows: $I_a = aV_g^2 \exp(-b\Phi^{3/2}/V_g)$, where a and b have the appropriate units. For example, a may be expressed in micro-Amperes per volt-squared (μA/$V^2$), and b may be expressed in reciprocal square-root volts ($V^{-1/2}$), where the anode current $I_a$ is expressed in micro-Amperes (μA), and the gate voltage $V_g$ and the work function $\Phi$ of the emitters 245 are both expressed in volts (V). As shown in FIG. 2(c), the reciprocal of the gate voltage $V_g$, measured in volts (V), is plotted along the horizontal axis against the natural logarithm of the anode current $I_a$ divided by a times the square of the gate voltage $V_g$, $I_a/a(V_g)^2$, plotted along the vertical axis. As shown in FIG. 2(c), the slope of the line is proportional to the cube of the square-root ($\Phi^{3/2}$) of the work function $\Phi$. The extraction efficiency can be controlled by the gate electrode 255.

In an electron impact ionization source (EIIS), the emitted electrons are accelerated to very high voltages. When the electrons collide with neutral gas atoms and/or molecules, the electrons transfer energy to the neutral gas atoms and/or molecules, leading to ionization of the gas atoms and/or molecules. The process can result in the fragmentation of the gas molecules, leading to several by-products with specific signatures. The ions may be spectrally separated by ion optics and detected by mass spectrometry. A field emission array (FEA) is an efficient low voltage and low-power electron source for a field ionization system.

An example of the effect of high electric fields and/or high electron flux densities on a simple molecule is the ionization of molecular oxygen, $O_2$, under these extreme conditions. In a conventional electron impact ionization source (EIIS), the predominant species formed is the molecular oxygen ion, $O_2^+$. In the presence of an "active" field emitter array (FEA), according to various illustrative embodiments of the present invention, the predominant species that is formed is the atomic oxygen ion, $O^+$.

Figure 3:
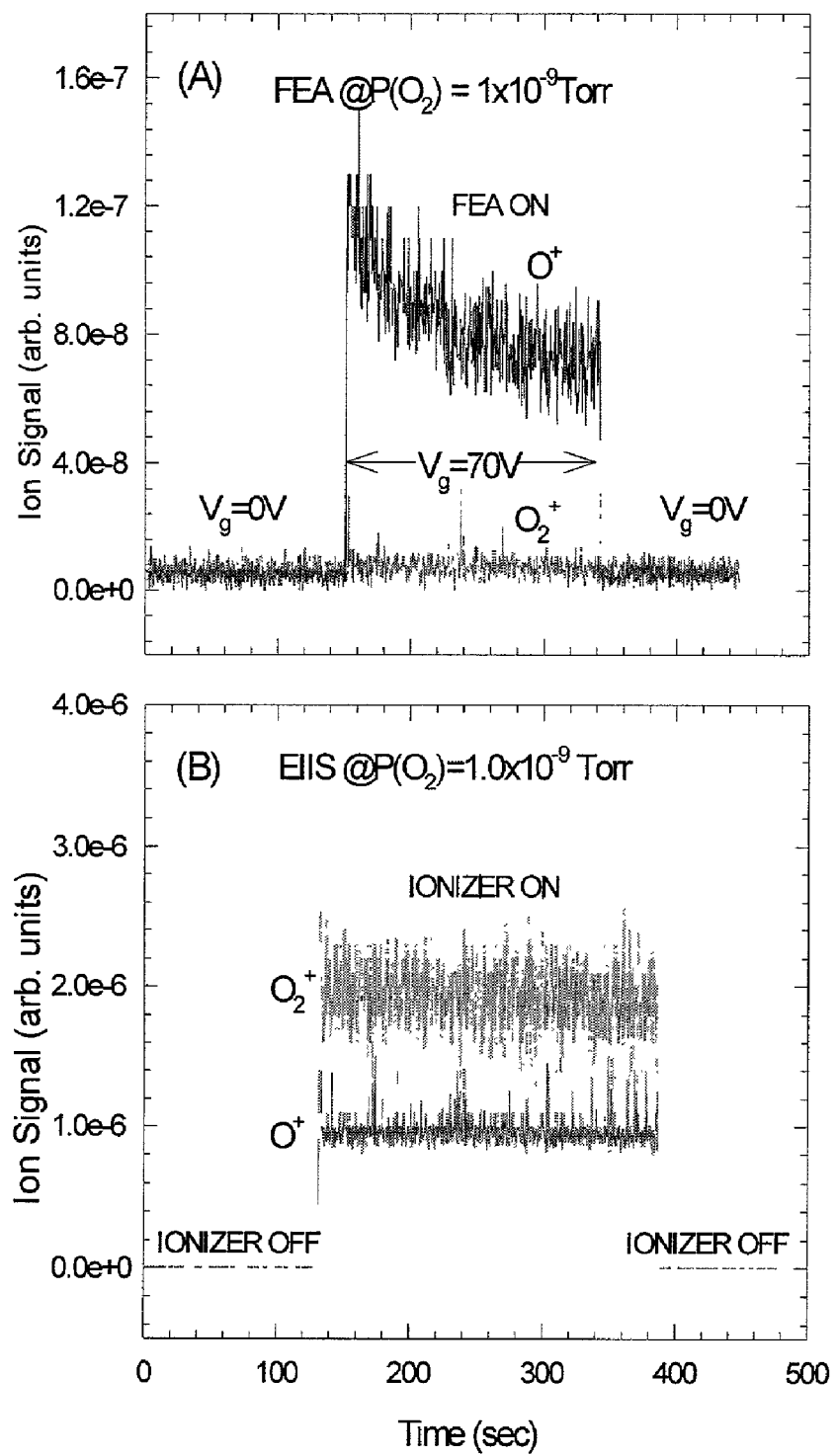

FIG. 3 shows the difference between the ionization from a field emitter array (FEA) and the ionization from a conventional electron impact ionization source (EIIS), under controlled vacuum conditions. The time, measured in seconds (sec), is plotted along the horizontal axis against an ion signal, measured in arbitrary units (arb. Units), plotted along the vertical axis. The pressure of the molecular oxygen $O_2$ for both sets of measurements is about $10^{-9}$ Torricellis (Torr), $P(O_2)=10^{-9}$ Torr.

In FIG. 3(a), the field emitter array (FEA) is initially exposed to molecular oxygen $O_2$ with the gate voltage off ($V_g=0$) to exhibit a reference signal (a partial pressure measurement) molecular oxygen of $O_2$. Subsequently, the gate voltage is increased to about 70 V ($V_g=70$ V) to "activate" the field emitter array (FEA), thus rendering field emitted electrons (similar to the field emitted electrons 260, as shown in FIG. 2(a)), under high electric field (electric field strength in a range of about $10^7$-$10^8$ V/cm) conditions. The dominant species observed is the atomic oxygen ion $O^+$, instead of the molecular oxygen ion $O_2^+$.

By way of contrast, FIG. 3(b) presents the results of a substantially similar experiment with a conventional electron impact ionization source (EIIS) configuration, where the molecular oxygen ion $O_2^+$ is the dominant species observed. The conventional electron impact ionization source (EIIS) ionizer in this experiment was "off" for about 100 sec, "on" for the next about 300 sec, and then "off" again thereafter. Given the substantially identical controlled vacuum conditions in which these measurements were obtained, it is unlikely that the molecular oxygen ion $O_2^+$ is scavenged by the activated field emitter array (FEA) to result in the observed $O^+$ abundance. Rather, in the presence of an activated field emitter array (FEA), according to various illustrative embodiments of the present invention, the predominant species formed is the atomic oxygen ion $O^+$.

Figure 4:
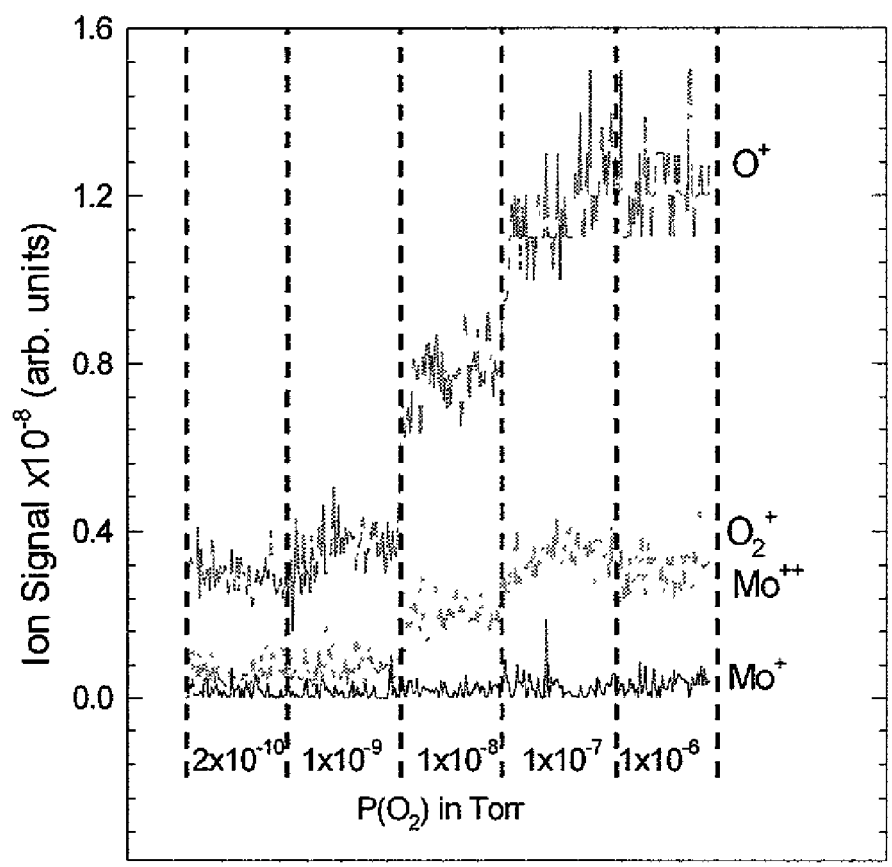

FIG. 4 shows a comparison of the production of the atomic oxygen ion $O^+$ and molecular oxygen ion $O_2^+$ as a function of the molecular oxygen $O_2$ pressure. The pressure $P(O_2)$ of the molecular oxygen $O_2$, measured in Torr, ranging from about $P(O_2)=2\times10^{-10}$ Torr to about $P(O_2)=1\times10^{-6}$ Torr, is plotted along the horizontal axis against an ion signal$\times10^{-8}$, measured in arbitrary units (arb. units), plotted along the vertical axis.

The atomic oxygen ion $O^+$ species remains dominant throughout the pressure regime examined. Moreover, ionized molybdenum ($Mo^+$ and $Mo^{++}$) species are also observed at higher molecular oxygen $O_2$ partial pressures, indicating that the tip undergoes modification, probably from the atomic oxygen ion $O^+$ species exposure, under active conditions of an activated field emitter array (FEA), according to various illustrative embodiments of the present invention.

Figure 5:
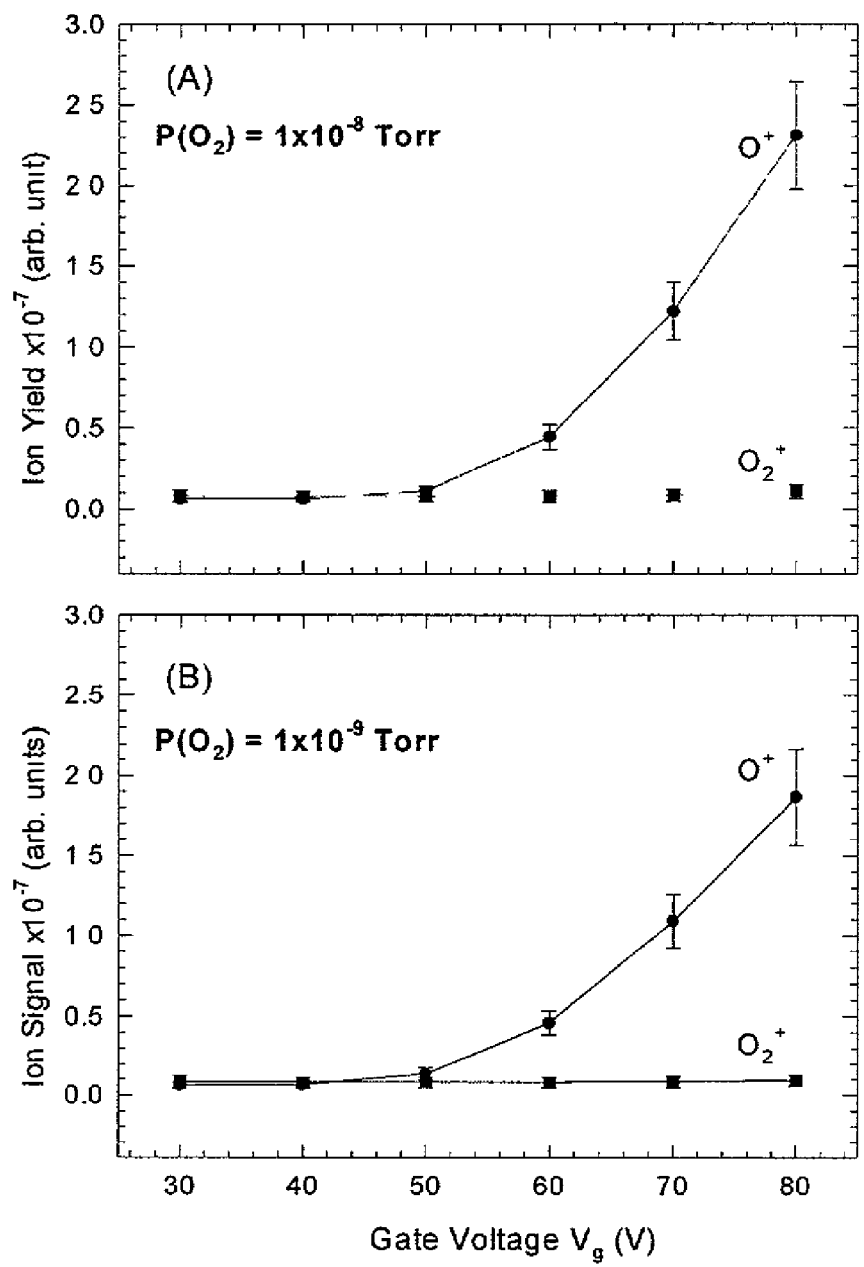

FIG. 5 shows a comparison of the production of the atomic oxygen ion $O^+$ and molecular oxygen ion $O_2^+$ as a function of gate voltage $V_g$. The gate voltage $V_g$, measured in volts (V), is plotted along the horizontal axis against an ion signal$\times10^{-7}$, measured in arbitrary units (arb. units), plotted along the vertical axis. In FIG. 5(a), the pressure $P(O_2)$ of the molecular oxygen $O_2$, measured in Torr, is about $P(O_2)=1\times10^{-8}$ Torr. In FIG. 5(b), the pressure $P(O_2)$ of the molecular oxygen $O_2$, measured in Torr, is about $P(O_2)=1\times10^{-9}$ Torr. Again, the atomic oxygen ion $O^+$ is observed as the dominant species above $V_g=50$ V. However, the comparison of the production of the atomic oxygen ion $O^+$ and molecular oxygen ion $O_2^+$ as a function of gate voltage $V_g$ is complicated by the fact that by raising the gate voltage $V_g$, the electric field strength $E_g$, and the Fowler-Nordheim tunneling anode current density $J_a$ (where $J_a$=the Fowler-Nordheim tunneling anode current $I_a$ per unit area, is essentially the electron emission 260 flux, in Amperes per square centimeter, for example), both increase concomitantly. Depending on the process for the formation of the atomic oxygen ion $O^+$, either of the parameters, the value of the electric field strength $E_g$, and/or the value of the Fowler-Nordheim tunneling anode current density $J_a$, may contribute to enhanced formation of the atomic oxygen ion $O^+$.

Figure 6:
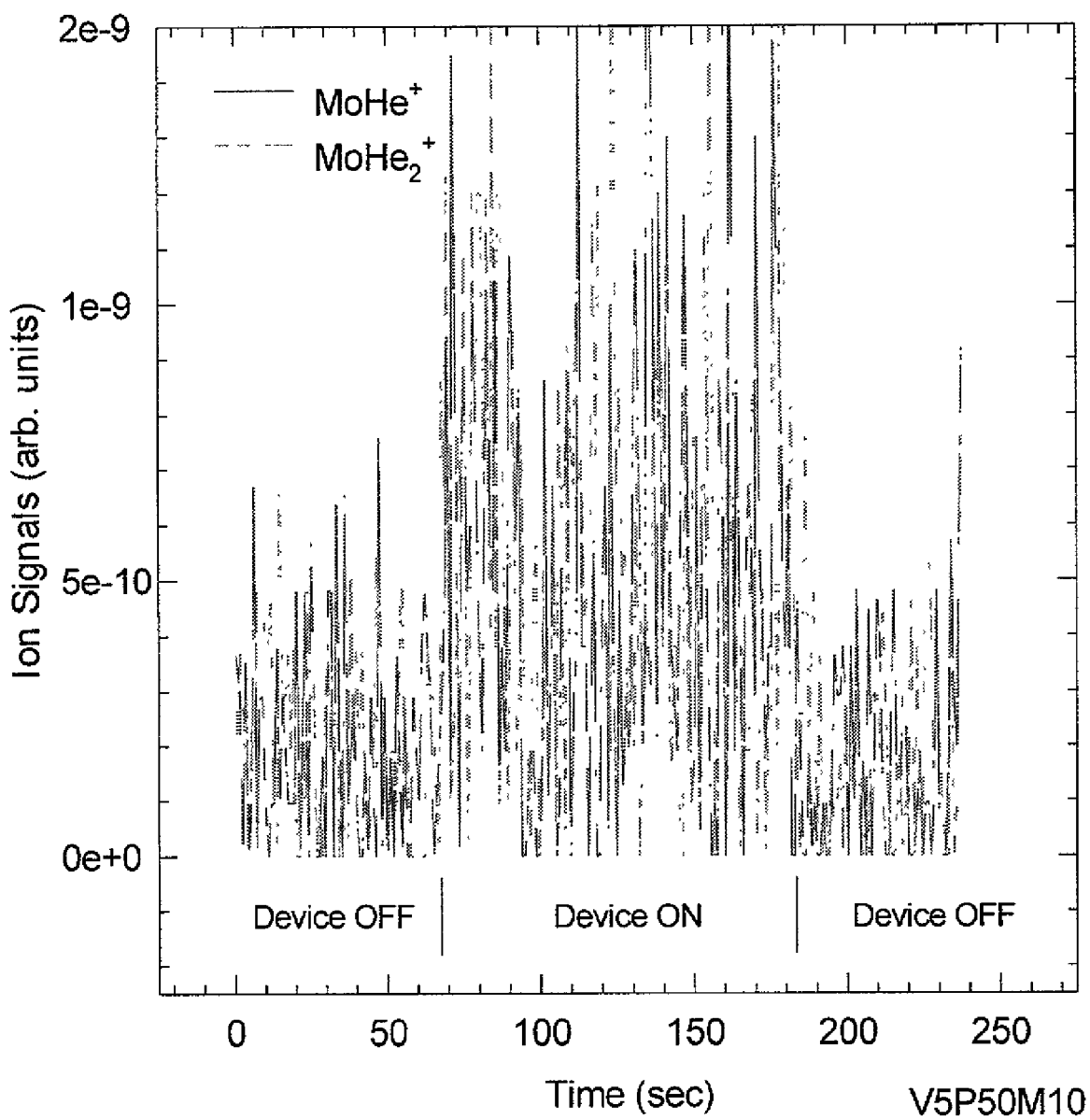

Interestingly, when a molybdenum-based field emitter array (FEA) is exposed to helium, molybdenum-helide ions such as $MoHe^+$ and $MoHe_2^+$ may be formed, as shown in FIG. 6. The time, measured in seconds (sec), is plotted along the horizontal axis against an ion signal, measured in arbitrary units (arb. Units), plotted along the vertical axis. The molybdenum-based field emitter array (FEA) in this experiment was "off" for about 70 sec, "on" for the next about 110 sec, and then "off" again thereafter.

Although the observation of molybdenum-helides was first reported by E. W. Mueller, in *Adv. Electr. Electron Phys.*, Vol. 13 (1960), at page 83, in early single-tip Field Ion Microscopy (FIM) studies, the poor ion counting statistics of the technique resulted in debates over the data for many years thereafter. The use of a field emission array (FEA) with about $10^5$ tips 240 (FIG. 2(a)), improves the sensitivity to such reaction channels, and thus permits a wider range of possibilities for observation and study of molybdenum-helide ions such as $MoHe^+$ and $MoHe_2^+$. It is believed that the lifetimes of the helide ion species, such as $MoHe^+$ and $MoHe_2^+$ is long enough to allow the molecular species to travel approximately 20 cm from the field emitter cathode 215 to a quadrupole mass spectrometer (not shown), where the ionic species may be detected.

Figure 7:
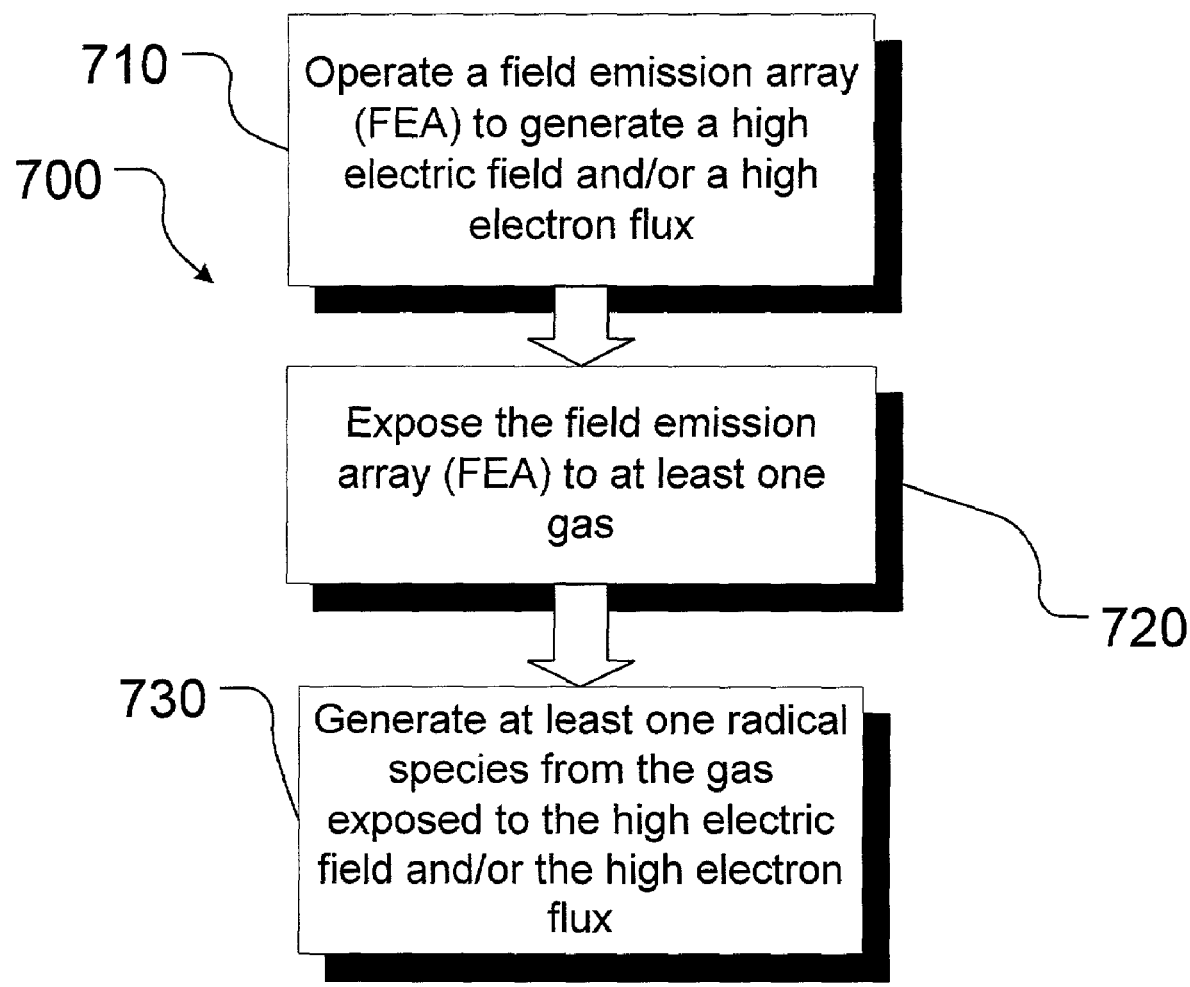

As shown in FIG. 7, in various illustrative embodiments of the present invention, a field emitter array (FEA), similar to the field emitter array (FEA) schematically illustrated in FIG. 2(a), is used to generate high electric fields and/or electron fluxes to generate a radical species resultant from the exposure of the electrically biased field emitter array (FEA) to candidate gases ($O_2$ being an example of a candidate gas). As shown in FIG. 7, a method 700 may be provided, the method 700 comprising operating a field emitter array (FEA) to generate at least one of a high electric field and/or a high electron flux, as shown in box 710.

Operating the field emitter array (FEA) to generate a high electric field and/or a high electron flux, as shown in box 710, may comprise operating the field emitter array (FEA) to generate an electric field having a field strength in a range of about $10^7$-$10^8$ V/cm. Operating the field emitter array (FEA) to generate a high electric field and/or a high electron flux, as shown in box 710, may comprise operating the field emitter array (FEA) to generate an electron flux in a range of about 0.5-2.0 Amp/cm². Operating the field emitter array (FEA) to generate a high electric field and/or a high electron flux, as shown in box 710, may comprise operating the field emitter array (FEA) with voltages of no more than about 100 V. In various alternative illustrative embodiments, operating the field emitter array (FEA) to generate a high electric field and/or a high electron flux, as shown in box 710, may comprise operating the field emitter array (FEA) with voltages of no more than about 1000 V with single wire emitters.

The method 700 further comprises exposing the field emitter array (FEA) to at least one gas, as shown in box 720. Exposing the field emitter array (FEA) to at least one gas, as shown in box 720, may comprise exposing the field emitter array (FEA) to molecular oxygen ($O_2$). The method 700 also comprises generating at least one radical species from the gas exposed to the high electric field and/or the high electron flux, as shown in box 730.

As shown in FIG. 8, in various alternative illustrative embodiments of the present invention, a low-power field emitter array (FEA), similar to the field emitter array (FEA) schematically illustrated in FIG. 2(*a*), is used to generate radical species to be made available to subsequently dissociate chemical or biological toxins and render them harmless or suitable for further reduction to a harmless state. As shown in FIG. 8, a method 800 may be provided, the method 800 comprising operating a low-power field emitter array (FEA) to generate at least one of a high electric field and/or a high electron flux, as shown in box 810.

Operating the low-power field emitter array (FEA) to generate a high electric field and/or a high electron flux, as shown in box 810, may comprise operating the low-power field emitter array (FEA) to generate an electric field having a field strength in a range of about $10^7$-$10^8$ V/cm. Operating the low-power field emitter array (FEA) to generate a high electric field and/or a high electron flux, as shown in box 810, may comprise operating the low-power field emitter array (FEA) to generate an electron flux in a range of about 0.5-2.0 Amp/cm$^2$. Operating the low-power field emitter array (FEA) to generate a high electric field and/or a high electron flux, as shown in box 810, may comprise operating the low-power field emitter array (FEA) with voltages of no more than about 100 V. In various alternative illustrative embodiments, operating the field emitter array (FEA) to generate a high electric field and/or a high electron flux, as shown in box 810, may comprise operating the field emitter array (FEA) with voltages of no more than about 1000 V with single wire emitters.

The method 800 further comprises exposing the low-power field emitter array (FEA) to at least one gas, as shown in box 820. Exposing the low-power field emitter array (FEA) to at least one gas, as shown in box 820, may comprise exposing the low-power field emitter array (FEA) to molecular oxygen ($O_2$).

The method 800 still further comprises generating at least one radical species from the gas exposed to the high electric field and/or the high electron flux, as shown in box 830. The method 800 also comprises reacting the radical species with at least one of a chemical and/or a biological toxin, as shown in box 840.

As shown in FIG. 9, in various alternative illustrative embodiments of the present invention, a low-power field emitter array (FEA), similar to the field emitter array (FEA) schematically illustrated in FIG. 2(*a*), is used to dissociate chemical and/or biological toxins directly and render them harmless and/or suitable for further reduction to a harmless state. As shown in FIG. 9, a method 900 may be provided, the method 900 comprising operating a low-power field emitter array (FEA) to generate at least one of a high electric field and/or a high electron flux, as shown in box 910.

Operating the low-power field emitter array (FEA) to generate a high electric field and/or a high electron flux, as shown in box 910, may comprise operating the low-power field emitter array (FEA) to generate an electric field having a field strength in a range of about $10^7$-$10^8$ V/cm. Operating the low-power field emitter array (FEA) to generate a high electric field and/or a high electron flux, as shown in box 910, may comprise operating the low-power field emitter array (FEA) to generate an electron flux in a range of about 0.5-2.0 Amp/cm$^2$. Operating the low-power field emitter array (FEA) to generate a high electric field and/or a high electron flux, as shown in box 910, may comprise operating the low-power field emitter array (FEA) with voltages of no more than about 100 V. In various alternative illustrative embodiments, operating the field emitter array (FEA) to generate a high electric field and/or a high electron flux, as shown in box 910, may comprise operating the field emitter array (FEA) with voltages of no more than about 1000 V with single wire emitters.

Operating the low-power field emitter array (FEA) to generate a high electric field and/or a high electron flux, as shown in box 910, may comprise operating the low-power field emitter array (FEA) with a cathode-to-gate distance of not more than about 1 micron (1 μm). In various alternative illustrative embodiments, operating the low-power field emitter array (FEA) to generate a high electric field and/or a high electron flux, as shown in box 910, may comprise operating the low-power field emitter array (FEA) with a cathode-to-gate distance and/or gate openings in a range of about 1 micron (1 μm) to about 1 millimeter (1 mm).

The method 900 further comprises exposing the low-power field emitter array (FEA) to at least one of a chemical and/or a biological toxin, as shown in box 920. The method 900 also comprises dissociating the chemical and/or the biological toxin exposed to the high electric field and/or the high electron flux, as shown in box 930.

As shown in FIG. 10, in various illustrative embodiments of the present invention, a field emitter array (FEA), similar to the field emitter array (FEA) schematically illustrated in FIG. 2(*a*), is used as an ionization source to facilitate the detection of biological and/or chemical toxins. As shown in FIG. 10, a method 1000 may be provided, the method 1000 comprising operating a field emitter array (FEA) to generate at least one of a high electric field and/or a high electron flux, as shown in box 1010.

Operating the low-power field emitter array (FEA) to generate a high electric field and/or a high electron flux, as shown in box 1010, may comprise operating the low-power field emitter array (FEA) to generate an electric field having a field strength in a range of about $10^7$-$10^8$ V/cm. Operating the low-power field emitter array (FEA) to generate a high electric field and/or a high electron flux, as shown in box 1010, may comprise operating the low-power field emitter array (FEA) to generate an electron flux in a range of about 0.5-2.0 Amp/cm$^2$. Operating the low-power field emitter array (FEA) to generate a high electric field and/or a high electron flux, as shown in box 1010, may comprise operating the low-power field emitter array (FEA) with voltages of no more than about 100 V. In various alternative illustrative embodiments, operating the field emitter array (FEA) to generate a high electric field and/or a high electron flux, as shown in box 1010, may comprise operating the field emitter array (FEA) with voltages of no more than about 1000 V with single wire emitters.

Operating the low-power field emitter array (FEA) to generate a high electric field and/or a high electron flux, as shown in box 1010, may comprise operating the low-power field emitter array (FEA) with a cathode-to-gate distance of not more than about 1 micron (1 μm). In various alternative illustrative embodiments, operating the low-power field emitter array (FEA) to generate a high electric field and/or a high electron flux, as shown in box 1010, may comprise operating the low-power field emitter array (FEA) with a cathode-to-gate distance and/or gate openings in a range of about 1 micron (1 μm) to about 1 millimeter (1 mm).

The method 1000 further comprises exposing the field emitter array (FEA) to at least one of a chemical and/or a biological toxin, as shown in box 1020. The method 1000 also comprises ionizing the chemical and/or the biological toxin exposed to the high electric field and/or the high electron flux, as shown in box 1030.

Most conventional biological and chemical warfare agent detection systems depend on a two-pass detection system. An ultraviolet (UV) fluorescence excitation/detection system is typically used to scan for a non-specific trigger to distinguish between biological and non-biological matter. This is followed by a time-of-flight (TOF) mass spectrometer that provides specific discrimination between various biological and chemical agents. These conventional biological and chemical warfare agent detection systems are typically rack mounted and may fill up a room, or at least a small vehicle. These conventional biological and chemical warfare agent detection systems consume significant power and require human interaction. Consequently, these conventional biological and chemical warfare agent detection systems are unsuitable for battlefield and emergency operations.

A study of conventional systems that are based on mass spectrometry suggests that there is a need for more compact, more sensitive, more stable and lower power methods of ionizing the pathogens and/or agents. As described herein, we have developed very compact and low-power detection systems with high sensitivity. Another issue that has plagued existing conventional systems is the reliability and the stability of the ionization sources. The ionization source is important to the development of compact, low-power, low cost and high sensitivity biological and chemical warfare agent detection systems. Also important is the use of field emitter arrays for the destruction of biological and chemical agents through the use of high field chemistry.

As described herein, we have developed new approaches to ionizing the biological and/or chemical agents with extremely low-power, low voltage, small size and high sensitivity suitable for compact instruments that can be deployed in the field. In order to use a field emitter array (FEA) for a field ionization source, it is desirable that such a field emitter array (FEA) operate robustly in a variety of environments.

Any of the above-disclosed embodiments of a method according to the present invention enables the size of biological and chemical toxin mitigation and/or remediation and/or detection systems to be reduced to tabletop and/or shoebox sizes. Any of the above-disclosed embodiments of a method according to the present invention enables such a system to be the size of the "Palm Pilot®" so that it may be carried by an individual soldier. Such a system that is more compact, operates in real-time and consumes less power, and could be deployed in remote locations, on a soldier, on an intelligent robot, or on an unmanned aerial vehicle (UAV) that is able to communicate with a base station. Corrective actions could be initiated with information supplied by such a system.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, in the sense of Georg Cantor. Accordingly, the protection sought herein is as set forth in the claims below.

What is claimed:

1. A method comprising:
   operating a low-power field emitter array (FEA) to generate at least one of a high electric field and a high electron flux;
   exposing the low-power field emitter array (FEA) to at least one gas;
   generating at least one radical species from the at least one gas exposed to the at least one of the high electric field and the high electron flux; and
   reacting the at least one radical species with at least one toxin.

2. The method of claim 1, wherein operating the low-power field emitter array (FEA) comprises operating the low-power field emitter array (FEA) to generate an electric field having a field strength in a range of about $10^7$-$10^8$ V/cm.

3. The method of claim 1, wherein operating the low-power field emitter array (FEA) comprises operating the low-power field emitter array (FEA) to generate an electron flux in a range of about 0.5-2.0 Amp/cm$^2$.

4. The method of claim 1, wherein operating the low-power field emitter array (FEA) comprises operating the low-power field emitter array (FEA) with voltages of no more than about 100 V.

5. The method of claim 1, wherein exposing the low-power field emitter array (FEA) to the at least one gas comprises exposing the low-power field emitter array (FEA) to molecular oxygen ($O_2$).

6. A method comprising:
   operating a low-power field emitter array (FEA) with voltages of no more than about 1000 V to generate at least one of a high electric field and a high electron flux;
   exposing the low-power field emitter array (FEA) to at least one gas;
   generating at least one radical species from the at least one gas exposed to the at least one of the high electric field and the high electron flux; and
   reacting the at least one radical species with at least one toxin.

7. The method of claim 6, wherein operating the low-power field emitter array (FEA) comprises operating the low-power field emitter array (FEA) to generate an electric field having a field strength in a range of about $10^7$-$10^8$ V/cm.

8. The method of claim 6, wherein operating the low-power field emitter array (FEA) comprises operating the low-power field emitter array (FEA) to generate an electron flux in a range of about 0.5-2.0 Amp/cm$^2$.

9. The method of claim 6, wherein operating the low-power field emitter array (FEA) comprises operating the low-power field emitter array (FEA) with voltages of no more than about 100 V.

10. The method of claim 6, wherein exposing the low-power field emitter array (FEA) to the at least one gas comprises exposing the low-power field emitter array (FEA) to molecular oxygen ($O_2$).

11. A method comprising:
    operating a low-power field emitter array (FEA) to generate at least one of a high electric field and a high electron flux;
    exposing the low-power field emitter array (FEA) to at least one toxin; and
    dissociating the at least one toxin exposed to the at least one of the high electric field and the high electron flux.

12. The method of claim 11, wherein operating the low-power field emitter array (FEA) comprises operating the low-power field emitter array (FEA) to generate an electric field having a field strength in a range of about $10^7$-$10^8$ V/cm.

13. The method of claim 11, wherein operating the low-power field emitter array (FEA) comprises operating the low-power field emitter array (FEA) to generate an electron flux in a range of about 0.5-2.0 Amp/cm$^2$.

14. The method of claim 11, wherein operating the low-power field emitter array (FEA) comprises operating the low-power field emitter array (FEA) with voltages of no more than about 100 V.

15. The method of claim 11, wherein operating the low-power field emitter array (FEA) comprises operating the low-power field emitter array (FEA) with a cathode-to-gate distance of not more than about 1 micron (1 μm).

16. A method comprising:
    operating a low-power field emitter array (FEA) with voltages of no more than about 1000 V to generate at least one of a high electric field and a high electron flux;
    exposing the low-power field emitter array (FEA) to at least one toxin; and
    dissociating the at least one toxin exposed to the at least one of the high electric field and the high electron flux.

17. The method of claim 16, wherein operating the low-power field emitter array (FEA) comprises operating the low-power field emitter array (FEA) to generate an electric field having a field strength in a range of about $10^7$-$10^8$ V/cm.

18. The method of claim 16, wherein operating the low-power field emitter array (FEA) comprises operating the low-power field emitter array (FEA) to generate an electron flux in a range of about 0.5-2.0 Amp/$cm^2$.

19. The method of claim 16, wherein operating the low-power field emitter array (FEA) comprises operating the low-power field emitter array (FEA) with voltages of no more than about 100 V.

20. The method of claim 16, wherein operating the low-power field emitter array (FEA) comprises operating the low-power field emitter array (FEA) with a cathode-to-gate distance of not more than about 1 micron (1 μm).

21. A method comprising:

operating a low-power field emitter array (FEA) with gate openings in a range of about 1 micron (1 μm) to about 1 millimeter (1 mm) to generate at least one of a high electric field and a high electron flux;

exposing the low-power field emitter array (FEA) to at least one toxin; and dissociating the at least one toxin exposed to the at least one of the high electric field and the high electron flux.

22. The method of claim 21, wherein operating the low-power field emitter array (FEA) comprises operating the low-power field emitter array (FEA) to generate an electric field having a field strength in a range of about $10^7$-$10^8$ V/cm.

23. The method of claim 21, wherein operating the low-power field emitter array (FEA) comprises operating the low-power field emitter array (FEA) to generate an electron flux in a range of about 0.5-2.0 Amp/$cm^2$.

24. The method of claim 21, wherein operating the low-power field emitter array (FEA) comprises operating the low-power field emitter array (FEA) with voltages of no more than about 100 V.

25. The method of claim 21, wherein operating the low-power field emitter array (FEA) comprises operating the low-power field emitter array (FEA) with a cathode-to-gate distance in a range of about 1 micron (1 μm) to about 1 millimeter (1 mm).

26. A method comprising:

operating a low-power field emitter array (FEA) with voltages of no more than about 1000 V with gate openings in a range of about 1 micron (1 μm) to about 1 millimeter (1 mm) to generate at least one of a high electric field and a high electron flux;

exposing the low-power field emitter array (FEA) to at least one toxin; and dissociating the at least one toxin exposed to the at least one of the high electric field and the high electron flux.

27. The method of claim 26, wherein operating the low-power field emitter array (FEA) comprises operating the low-power field emitter array (FEA) to generate an electric field having a field strength in a range of about $10^7$-$10^8$ V/cm.

28. The method of claim 26, wherein operating the low-power field emitter array (FEA) comprises operating the low-power field emitter array (FEA) to generate an electron flux in a range of about 0.5-2.0 Amp/$cm^2$.

29. The method of claim 26, wherein operating the low-power field emitter array (FEA) comprises operating the low-power field emitter array (FEA) with voltages of no more than about 100 V.

30. The method of claim 26, wherein operating the low-power field emitter array (FEA) comprises operating the low-power field emitter array (FEA) with a cathode-to-gate distance in a range of about 1 micron (1 μm) to about 1 millimeter (1 mm).

31. A method comprising:

operating a field emitter array (FEA) to generate at least one of a high electric field and a high electron flux;

exposing the field emitter array (FEA) to at least one toxin; and ionizing the at least one toxin exposed to the at least one of the high electric field and the high electron flux.

32. The method of claim 31, wherein operating the field emitter array (FEA) comprises operating the field emitter array (FEA) to generate an electric field having a field strength in a range of about $10^7$-$10^8$ V/cm.

33. The method of claim 31, wherein operating the field emitter array (FEA) comprises operating the field emitter array (FEA) to generate an electron flux in a range of about 0.5-2.0 Amp/$cm^2$.

34. The method of claim 31, wherein operating the field emitter array (FEA) comprises operating the field emitter array (FEA) with voltages of no more than about 100 V.

35. The method of claim 31, wherein operating the field emitter array (FEA) comprises operating the field emitter array (FEA) with a cathode-to-gate distance of not more than about 1 micron (1 μm).

36. A method comprising:

operating a field emitter array (FEA) with voltages of no more than about 1000 V to generate at least one of a high electric field and a high electron flux;

exposing the field emitter array (FEA) to at least one toxin; and ionizing the at least one toxin exposed to the at least one of the high electric field and the high electron flux.

37. The method of claim 36, wherein operating the field emitter array (FEA) comprises operating the field emitter array (FEA) to generate an electric field having a field strength in a range of about $10^7$-$10^8$ V/cm.

38. The method of claim 36, wherein operating the field emitter array (FEA) comprises operating the field emitter array (FEA) to generate an electron flux in a range of about 0.5-2.0 Amp/cm$^2$.

39. The method of claim 36, wherein operating the field emitter array (FEA) comprises operating the field emitter array (FEA) with voltages of no more than about 100 V.

40. The method of claim 36, wherein operating the field emitter array (FEA) comprises operating the field emitter array (FEA) with a cathode-to-gate distance of not more than about 1 micron (1 μm).

41. A method comprising:
operating a field emitter array (FEA) with gate openings in a range of about 1 micron (1 μm) to about 1 millimeter (1 mm) to generate at least one of a high electric field and a high electron flux;
exposing the field emitter array (FEA) to at least one toxin; and
ionizing the at least one toxin exposed to the at least one of the high electric field and the high electron flux.

42. The method of claim 41, wherein operating the field emitter array (FEA) comprises operating the field emitter array (FEA) to generate an electric field having a field strength in a range of about $10^7$-$10^8$ V/cm.

43. The method of claim 41, wherein operating the field emitter array (FEA) comprises operating the field emitter array (FEA) to generate an electron flux in a range of about 0.5-2.0 Amp/cm$^2$.

44. The method of claim 41, wherein operating the field emitter array (FEA) comprises operating the field emitter array (FEA) with voltages of no more than about 100 V.

45. The method of claim 41, wherein operating the field emitter array (FEA) comprises operating the field emitter array (FEA) with a cathode-to-gate distance in a range of about 1 micron (1 μm) to about 1 millimeter (1 mm).

46. A method comprising:
operating a field emitter array (FEA) with voltages of no more than about 1000 V with gate openings in a range of about 1 micron (1 μm) to about 1 millimeter (1 mm) to generate at least one of a high electric field and a high electron flux;
exposing the field emitter array (FEA) to at least one toxin; and
ionizing the at least one toxin exposed to the at least one of the high electric field and the high electron flux.

47. The method of claim 46, wherein operating the field emitter array (FEA) comprises operating the field emitter array (FEA) to generate an electric field having a field strength in a range of about $10^7$-$10^8$ V/cm.

48. The method of claim 46, wherein operating the field emitter array (FEA) comprises operating the field emitter array (FEA) to generate an electron flux in a range of about 0.5-2.0 Amp/cm$^2$.

49. The method of claim 46, wherein operating the field emitter array (FEA) comprises operating the field emitter array (FEA) with voltages of no more than about 100 V.

50. The method of claim 46, wherein operating the field emitter array (FEA) comprises operating the field emitter array (FEA) with a cathode-to-gate distance in a range of about 1 micron (1 μm) to about 1 millimeter (1 mm).

51. A method comprising:
operating a low-power field emitter array (FEA) to generate at least one of a high electric field and a high electron flux;
exposing the low-power field emitter array (FEA) to at least one gas;
generating at least one radical species from the at least one gas exposed to the at least one of the high electric field and the high electron flux; and
reacting the at least one radical species with at least one of Sarin, Soman, arsine, germane, diborane, and a toxic chemical used in the production of at least one of ammonia ($NH_3$), chlorine ($Cl_2$), and an insecticide.

52. The method of claim 51, wherein operating the low-power field emitter array (FEA) comprises operating the low-power field emitter array (FEA) to generate an electric field having a field strength in a range of about $10^7$-$10^8$ V/cm.

53. The method of claim 51, wherein operating the low-power field emitter array (FEA) comprises operating the low-power field emitter array (FEA) to generate an electron flux in a range of about 0.5-2.0 Amp/cm$^2$.

54. The method of claim 51, wherein operating the low-power field emitter array (FEA) comprises operating the low-power field emitter array (FEA) with voltages of no more than about 100 V.

55. The method of claim 51, wherein exposing the low-power field emitter array (FEA) to the at least one gas comprises exposing the low-power field emitter array (FEA) to molecular oxygen ($O_2$).

56. A method comprising:
operating a low-power field emitter array (FEA) to generate at least one of a high electric field and a high electron flux;
exposing the low-power field emitter array (FEA) to at least one gas comprising at least one of a pathogen and a toxin; and
rendering said at least one of the pathogen and the toxin harmless in response to exposure of said at least one of the pathogen and the toxin to the low-power field emitter array (FEA).

57. The method of claim 56, wherein operating the low-power field emitter array (FEA) comprises operating the low-power field emitter array (FEA) to generate an electric field having a field strength in a range of about $10^7$-$10^8$ V/cm.

58. The method of claim 56, wherein operating the low-power field emitter array (FEA) comprises operating the low-power field emitter array (FEA) to generate an electron flux in a range of about 0.5-2.0 Amp/cm$^2$.

59. The method of claim 56, wherein operating the low-power field emitter array (FEA) comprises operating the low-power field emitter array (FEA) with voltages of no more than about 100 V.

60. The method of claim 56, wherein exposing the low-power field emitter array (FEA) to the at least one gas comprises exposing the low-power field emitter array (FEA) to molecular oxygen ($O_2$).

* * * * *